United States Patent [19]

Sigwalt et al.

[11] 4,161,494
[45] Jul. 17, 1979

[54] BI-AND TRIFUNCTIONAL ORGANOLITHIUM INITIATORS

[75] Inventors: Pierre Sigwalt, Saint Michel sur Orge; Patrick Guyot, Paris; Michel Fontanille, Montmorency, all of France

[73] Assignees: Societe Chimique des Charbonnages CDF Chimie, Paris; Agence Nationale de Valorisation de la Recherche, Neully sur Seine, both of France

[21] Appl. No.: 807,484

[22] Filed: Jun. 17, 1977

[30] Foreign Application Priority Data

Jun. 17, 1976 [FR] France .............................. 76 18453

[51] Int. Cl.² .............................................. C07F 1/02
[52] U.S. Cl. .............................................. 260/665 R
[58] Field of Search ................................... 260/665 R

[56] References Cited

U.S. PATENT DOCUMENTS

| 3,078,254 | 2/1963 | Zelinski et al. | 260/45.5 |
| 3,108,994 | 10/1963 | Zelinski et al. | 260/93.5 |
| 3,157,604 | 11/1964 | Strobel | 252/431 R |
| 3,208,988 | 9/1965 | Forman et al. | 260/94.2 |
| 3,287,333 | 11/1966 | Zelinski | 260/83.7 |
| 3,450,795 | 6/1969 | Langer | 260/878 |
| 3,668,263 | 6/1972 | Morrison et al. | 260/665 R |
| 3,725,368 | 4/1973 | Morrison et al. | 260/665 R |
| 3,734,973 | 5/1973 | Farrar | 260/665 R |
| 3,776,964 | 12/1973 | Morrison et al. | 260/665 R |
| 3,862,251 | 1/1975 | Strecker | 260/665 R |
| 3,903,168 | 9/1975 | Foss | 260/583 R |
| 3,954,894 | 5/1976 | Kamienski et al. | 260/665 R |
| 4,067,917 | 1/1978 | Sigwalt et al. | 260/665 R |

*Primary Examiner*—Helen M. S. Sneed

*Attorney, Agent, or Firm*—Finnegan, Henderson, Farabow & Garrett

[57] ABSTRACT

New organo-lithium initiators, their synthesis, and their use. The initiators have the formula:

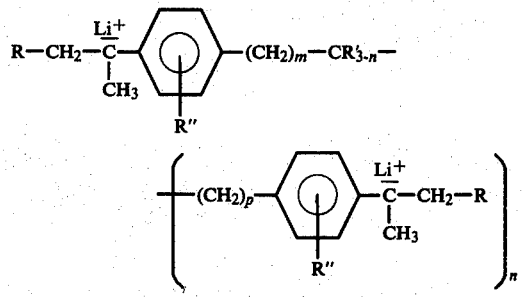

in which R" is either a hydrogen atom or a methyl radial; either n is 1, in which case R'=H and m and p are integers, the sum of which is between 0 and 10 inclusive, or n is 2, R' then being an alkyl radical of 2 to 8 carbon atoms and m =p =0; and R is an alkyl radical of 1 to 4 carbon atoms.

The initiators are prepared by reacting compounds of the formula:

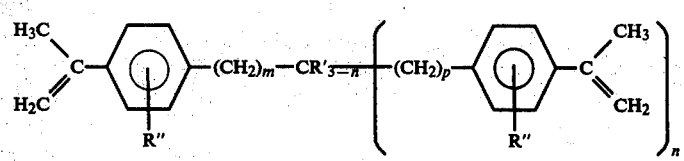

with an alkyl-lithium RLi in a non-polar solvent in the absence of any polar solvent or complexing agent.

The initiators are used to prepare polydienes of high stereoregularity by reacting with a diene, and the polydiene is used to prepare a three-block or star copolymer by reacting with an anionically polymerizable monomer.

3 Claims, No Drawings

BI-AND TRIFUNCTIONAL ORGANOLITHIUM INITIATORS

The present invention relates to the field of polymerization and copolymerization of unsaturated monomers using new bifunctional and trifunctional organo-lithium initiators.

It is well known to manufacture various polymers by polymerizing or copolymerizing unsaturated monomers by means of organo-lithium initiators. Those skilled in the art know that there are three different ways by which ABA block copolymers, wherein B is a diene and A is an anionically polymerizable monomer, can be obtained, depending on the type of initiator used:

(1) A process in three stages consisting of the successive addition of the monomer A, then the diene B and the monomer A again.

(2) A process in two stages consisting of forming a copolymer AB, in which B has a reactive end group, and subsequently coupling these reactive copolymers of the AB type with one another in order to form the three-block copolymer ABA.

These first two processes have the disadvantage that some homopolymers A and B and/or copolymer AB are produced. This latter product has a considerable effect on the mechanical properties.

(3) A process in two stages consisting of the use of a bifunctional initiator. However, the synthesis of this initiator has previously required the presence of polar and/or complexing agents, which proved to have an adverse effect in subsequent polymerization reactions, and the functionality was frequently imprecise, which again led to the formation of the copolymer AB.

The subject of the invention is, therefore, the synthesis of new organo-lithium initiators which are strictly bifunctional and trifunctional and which enable polydienes having bifunctional and trifunctional reactive end groups to be manufactured.

The invention also relates to polymers containing a polydiene block, the stereoregularity of which is at least equal to that of polydienes obtained by conventional means, as well as to derivatives of these polymers which carry, at their ends, reactive functional groups such as hydroxyl, acid, mercapto or peroxide. These latter products are polymers with terminal chelating groups. The three-block or star copolymers in which the central block is a polydiene and the outer blocks are formed from an anionically polymerizable monomer are thermoplastic elastomers with improved mechanical properties. Particularly interesting examples of such copolymers are those in which the central block is a polydiene, such as polyisoprene or polybutadiene, and the outer blocks are styrene polymers, methyl methacrylate polymers, α-methyl-styrene polymers, ethylene polymers or ethylene oxide polymers.

The first stage of the invention comprises the synthesis of compounds of the formula:

in which R″ is either a hydrogen atom or a methyl radical and either n is 1, in which case R′ = H and m and p are integers, the sum of which is between 0 and 10 inclusive, or n is 2, R′ then being an alkyl radical of 2 to 8 carbon atoms and m = p = 0.

The compounds of the formula (A) in which n = 1 are already known and their synthesis has been described, especially in U.S. Pat. No. 2,957,036. The new compounds of the formula (A) in which n = 2 are prepared according to a known method by a sequence of three stages:

reaction of a triphenylmethane derivative with an alkyl halide in the presence of diethyl ether and n-butyl-lithium in order to form a compound:

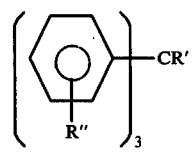

reaction of this compound with an acetyl halide in the presence of an aluminum trihalide and of carbon disulphide in order to form the triketone:

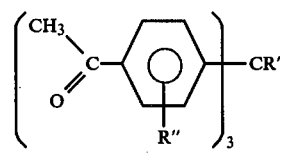

and a Wittig reaction of the triketone with a bromine-containing tri-phenyl-methylphosphonium derivative in the presence of dimethylsulphoxide and sodium hydride.

Characteristics common to the new products of the formula:

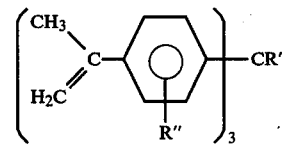

are the absorption maximum in ultraviolet light ($\lambda_{max}$ = 252 nm, $\epsilon_{max}$ = 3.05 × 10$^4$ mol$^{-1}$ · liter · cm.$^{-1}$) and the presence in the NMR spectrum of two signals typical of vinyl protons ($\delta$/TMS = 5.4 and 5.6 ppm). Each of these products can, moreover, be characterised by its melting point (28° C. for 1,1,1-tris-(4-isopropenyl-phenyl)-ethane) or its boiling point.

The second stage of the invention comprises the synthesis of compounds of the formula:

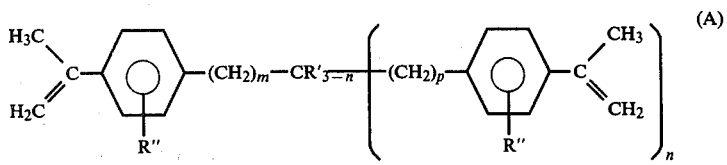

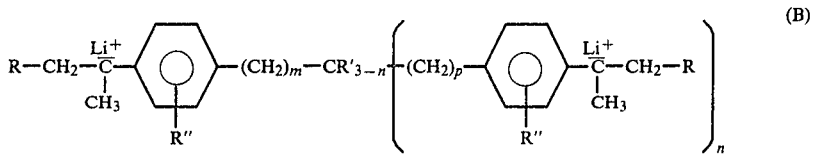

in which R'', R', m, p and n have the meanings already mentioned and R is an alkyl radical.

The new compounds of the formula (B) are prepared by reacting an alkyl-lithium RLi on the one hand with a compound of the formula (A) on the other hand, in a non-polar solvent medium, such as a saturated or aromatic hydrocarbon, the molar ratio of the alkyl-lithium to the compound (A) being greater than or equal to n so that the reaction equilibrium shifts by precipitation of the desired bifunctional or trifunctional organo-lithium compound.

For reasons of stability, it is preferable to work at temperatures lower than 40° C., under normal pressure. In practice, however, the reaction is carried out at ambient temperature. The pressure can be lower or higher than atmospheric pressure, within the limits of 0 to 100 bars; for reasons of simplicity, however, the reaction is carried out under atmospheric pressure.

Taking into account the sensitivity of the products taking part in the reaction, it is essential to carry out the reaction in the absence of atmospheric impurities (oxygen, $H_2O$, $CO_2$ and the like). The reaction is therefore carried out in vacuo or in an atmosphere of a gas which is inert towards the reactants, for example in an argon or nitrogen atmosphere.

The reaction is continued until the entire amount of compound A has reacted with the alkyl-lithium. The reaction can optionally be adapted to continuous operation, the organo-lithium compound then being drawn off continuously at the rate at which it is formed.

Whatever the means by which the invention is carried out, that is, whether batch or continuous, the excess alkyl-lithium is removed by filtering the reaction mixture. The organo-lithium compound (B) is obtained in the form of a precipitate, and this is washed at least once, preferably with the solvent distilled from the reaction medium, in order to obtain a purity on the order of 98%. Above this value, the traces of impurities are not detrimental during subsequent use of the compound, especially when the compound is used as a polymerization initiator.

Common characteristics of the new products of the formula (B) are their absorption maximum in ultraviolet light:

$\lambda_{max}$ = 335 nm and $\epsilon_{max}$ = 2.2 × $10^4$ $mol^{-1}$ - liter -$cm.^{-1}$ when n = 1

$\lambda_{max}$ = 340 nm and $\epsilon_{max}$ = 3.6 × $10^4$ $mol^{-1}$ - liter -$cm.^{-1}$ when n = 2.

The third stage of the invention comprises the homopolymerization reactions carried out using the compounds (B) as initiators. The novelty of this stage lies in the fact that the use of a polar and/or complexing compound is not called for in the course of the synthesis of the initiator (B). In the method previously used, the bifunctional or trifunctional organo-lithium compounds had to be prepared in the presence of ethers or tertiary amines. If such agents are used, they are always present together with the polymerization initiator and lead to less advantageous results during subsequent polymerization reactions. For example, the presence of polar and/or complexing agents leads, during the polymerization of dienes, to 1,2-linkages and, for example, in the case of isoprene, to a polymer consisting mainly of 3,4- and 1,4-trans-units, which are not advantageous for the production of good elastomers.

As in the prior art, the initiator (B) is insoluble in pure hydrocarbons. In order to overcome the disadvantages of a polymerization reaction in a heterogeneous medium, (B) is reacted with a small quantity of a diene, so that ultimately a polydiene which has reactive groups at its two ends and is soluble at a degree of polymerization of about 30 is obtained.

When the polydispersity of this polymer obtained from the above deactivated oligomers is checked by gel permeation chromatography, a chromatogram with a single peak is obtained and it is found that the weights of the macromolecules show little scatter. This implies that only one species has been responsible for the propagation of the polymerization.

Examples of dienes of this type are butadiene, isoprene, 2,3-dimethyl-butadiene and 1,3-pentadiene. The reaction temperature is preferably lower than 100° C.; the reaction medium is a non-polar solvent of the type already indicated above (saturated or aromatic hydrocarbon), such as pentane, hexane, heptane, benzene or toluene.

A polydiene which has bifunctional or trifunctional reactive end groups is thus obtained, the stereoregularity of which is at least equal to that of polydienes obtained by conventional means (the proportion of the 1,4-cis form, measured by nuclear magnetic resonance, is greater than or equal to 70%), and this polydiene is itself able to react in various ways. By way of example, it is possible to add ethylene oxide units in order to convert the end groups of the polydiene into diol and triol functional groups which can be used in the manufacture of polyurethanes. The polydiene can be converted into a di- or tri-carboxylic acid by treatment with $CO_2$. The polydiene is converted into a peroxide by an addition reaction with oxygen.

The fourth stage of the invention comprises the copolymerization reactions of anionically polymerizable monomers, such as those which have been defined above, by means of these polydienes having difunctional or trifunctional reactive groups, used as initiators, and optionally in the presence of at least one complexing agent and/or polar solvent. The complexing agents which can be used according to the invention are, in particular, tertiary amines and diamines, non-cyclic ethers, macrocyclic ethers, microbicyclic ethers or cryptates. Polar solvents which can be used according to the invention are, in particular, diethyl ether, tetrahydrofurane and hexamethylphosphotriamide.

Three-block or star copolymers of the ABA type, wherein A denotes a block such as an ethylene or styrene block, while the central block B is a polydiene, are thus obtained. The thermo-mechanical properties of these copolymers, which belong to the group of thermoplastic elastomers, are superior to those of the products previously obtained. They are, in fact, true copolymers.

The invention will now be illustrated by the nonlimiting examples which follow:

EXAMPLE 1

35 cm³ of a 1.6 M solution of n-butyl-lithium in hexane and 18 cm³ of trimethylethylenediamine are added to an ethereal solution of 12.2 g of triphenylmethane. The solution turns blood-red immediately. After stirring for 10 minutes, 0.05 mol of methyl iodide in 50 cm³ of ether are added slowly at 0° C. The solution loses its color and stirring is continued for one hour. The lithium iodide which has precipitated is then removed and washed with ether. The organic phases are combined and washed with acidified water. The ethereal solution is dried over $CaCl_2$ and evaporated, and the product is twice recrystallised from ethanol. This gives 1,1,1-triphenyl-ethane with a melting point of 94° C. in a yield of 80%.

17.62 g of aluminum bromide in 50 cm³ of carbon disulphide are added to a three-necked flask fitted with a condenser, a dropping funnel and a nitrogen inlet, and the mixture is left to stand until everything has dissolved. While maintaining the temperature at about 10° C., 7.4 g of acetyl bromide are added slowly. At the end of the addition, the mixture is heated under reflux for 30 minutes. It is then cooled by means of an ice/water bath and a solution of carbon disulphide containing 1,1,1-triphenylethane is added. The carbon disulphide is then distilled and the hydrolysis is carried out with acidified water; a thick oil floats on the surface. This is dried and the 1,1,1-tris-(4-acetyl-phenyl)-ethane, obtained in a yield of 60%, is used without further purification.

Triphenyl-methyl-phosphonium bromide is prepared: 200 ml of anhydrous benzene are poured into a round-bottomed flask fitted with a dropping funnel and a stirrer, and 157.5 g of triphenylphosphine are then dissolved in the benzene. 45.5 cm³ of methyl bromide are added at a temperature of −15° C. The temperature is allowed to return to room temperature and the mixture is stirred for 72 hours. The white precipitate is collected and is washed with 500 ml of hot benzene. It is dried in a vacuum drying cabinet at 100° C. for 24 hours. Triphenyl-methyl-phosphonium bromide with a melting point of 232.5° C. is obtained in a yield of 99%. A stream of anhydrous nitrogen is passed through all parts of the apparatus, which consists of a one liter three-necked flask fitted with a condenser, a dropping funnel, a stirrer and a gas inlet, during the entire operation. Triphenyl-methyl-phosphonium bromide is added to an ethereal solution of n-butyl-lithium (0.2 mol). The solution is added in the course of 4 hours at room temperature and a yellow-orange solution is obtained. 1,1,1-tris-(4-acetylphenyl)-ethane is added. The solution loses its color. The mixture is heated under reflux for 24 hours and the precipitate (unreacted triketone and phosphine oxide) is filtered off when the solution is at room temperature. It is washed with diethyl ether and then with petroleum ether. The solution is passed twice through a column of activated alumina. The physical characteristics of the 1,1,1-tris-(4-isopropenylphenyl)-ethane thus obtained in a yield of 30% are as follows:

melting point: 28° C. (very oily solid)
ultraviolet spectrum in hexane: $\lambda_{max}$ = 252 nm and $\epsilon_{max}$ = 30,500 mols$^{-1}$ -liter -cm.$^{-1}$.

EXAMPLE 2

All operations are carried out in the absence of atmospheric air. 1,1,1-tris-(4-isopropenyl-phenyl)-ethane (compound A) is purified by dissolving it in hexane and repeatedly passing the solution obtained over sodium. In the same way, tertiary-butyl-lithium is purified by sublimation in vacuo and then dissolved in hexane. The solution of compound (A) is introduced into a round-bottomed flask fitted with a quartz cell for spectrophotometry, and the solution of tertiary-butyl-lithium, the concentration of which is five to ten times that of (A), is then added. After rinsing the walls, the apparatus is sealed and plunged into a thermostat-controlled bath at 30° C. The solution becomes yellow within a few minutes and then, after several hours, a fine red precipitate appears and settles at the bottom of the flask. After three days at room temperature, the concentrations measured by spectrophotometry no longer change. The apparatus is then ready to be connected to that for the oligomerisation of the dienes.

EXAMPLE 3

The initiator obtained according to Example 2 was used for the stereospecific polymerization of a diene chosen by way of example, i.e., isoprene; the reaction medium was hexane.

The procedure employed also served to verify the functionality of the polyisopropenyl-lithium. In fact, it is known that, in polymerization by an anionic mechanism, the number-average weight, in the case of a trifunctional initiator, related to the amount of initiator and of the monomer, is given by the formula:

$$M_n = \frac{3\,m}{c}$$

wherein m denotes the amount of monomer and c denotes the amount of initiator. In practice, m is determined by a gravimetric method and c is determined by a spectrophotometric method.

In tests A, B and C of the table below, m and c were varied and an excellent agreement was found between the theoretical values and the experimental values of $M_n$ (determined by osmometry).

The various results given below show that the trifunctional initiator of Example 2 can be used in a pure hydrocarbon medium as an initiator for homopolymerization by an anionic mechanism.

Tests relating to the microstructure of the polyisoprenes obtained were carried out. The proportions of the different types of units present in the macromolecules were thus determined by analysing the 100 MHz NMR spectra for carbon and the ¹H proton. These proportions for test B are also indicated in the table below:

| TEST | $M_n$ | 1,4-cis | 1,4-trans | 3,4 |
|------|---------|---------|-----------|-----|
| A    | 60,000  |         |           |     |
| B    | 107,000 | 70      | 24        | 6   |
| C    | 240,000 |         |           |     |

EXAMPLE 4

All operations are carried out in the absence of atmospheric air. 1,2-bis-(4-isopropenyl-phenyl)-ethane (compound A), prepared in a known manner, for example according to U.S. Pat. No. 2,957,036, is purified by dissolving it in hexane and repeatedly passing the solution obtained over sodium. In the same way, tertiary butyl-lithium is purified by sublimation in vacuo and then dissolved in hexane. 1,2-[4-(1,3,3-trimethyl-1-lithium-butyl)-phenyl]-ethane is formed by mixing these two solutions under the conditions of Example 2.

EXAMPLE 5

First it is confirmed that the compound prepared according to Example 4 is up to about 98% free from monofunctional types. For this purpose, the compound can be washed with hexane and the increase in optical density at 335 nm determined. Isoprene is then brought into contact with the initiator. The precipitate becomes soluble in the unreacted isoprene. A polyisoprene having reactive groups at both ends is thus recovered and brought into the presence of tetramethylethylenediamine (in a molar ratio essentially equal to 2, relative to lithium) and ethylene for a time t. The number-average molecular weights of the central polydiene block ($M_1$) and of the resulting copolymer ($M_2$) are then determined by gel permeation chromatography; the proportion of units derived from ethylene (% E) in the copolymer is determined by nuclear magnetic resonance of the proton. The table below also shows the concentration of lithium in the polymerization medium. It is apparent from the results of test F that a chain-stopping reaction takes place at the same time as the initiation of ethylene on the polyisopropenyl-dilithium.

| TEST | t(hours) | Li mol/l | $M_1$ | $M_2$ | % E |
|------|----------|----------|-------|-------|-----|
| D | 19 | $2 \times 10^{-4}$ | 9,400 | 9,400 | 0 |
| F | 29.5 | $1.5 \times 10^{-3}$ | 55,000 | 57,000 | 11 |
| G | 24 | $3 \times 10^{-2}$ | 4,000 | 3,500 | 12 |

-continued

| TEST | t(hours) | Li mol/l | $M_1$ | $M_2$ | % E |
|------|----------|----------|-------|-------|-----|
| H | 22 | $3.4 \times 10^{-2}$ | 2,750 | 2,750 | 10.7 |

What is claimed is:
1. Products of the formula:

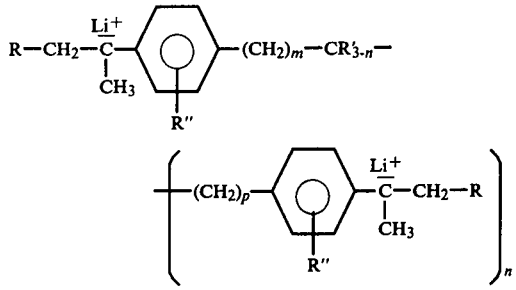

in which R" is either a hydrogen atom or a methyl radical and either n is 1, in which case R' = H and m and p are integers, the sum of which is between 0 and 10 inclusive, or n is 2, R' then being an alkyl radical of 2 to 8 carbon atoms and m = p = 0, and in which R is an alkyl radical of 1 to 4 carbon atoms, their absorption maximum in ultraviolet light being characterised by:
 (i) a wavelength of 335 nm and a molar extinction coefficient of $2.2 \times 10^4$ mols$^{-1}$-liter-cm.$^{-1}$ when n = 1 and
 (ii) a wavelength of 340 nm and a molar extinction coefficient of $3.6 \times 10^4$ mols$^{-1}$-liter-cm.$^{-1}$ when n = 2.

2. A product according to claim 1, which is the reaction product of 1,1,1-tris-(4-isopropenyl-phenyl)-ethane and tertiary-butyl-lithium.

3. A product according to claim 1, which is 1,2-[4-(1,3,3-trimethyl-1-lithium-butyl)-phenyl]-ethane.

* * * * *

UNITED STATES PATENT AND TRADEMARK OFFICE
CERTIFICATE OF CORRECTION

PATENT NO. : 4,161,494
DATED : July 17, 1979
INVENTOR(S) : PIERRE SIGWALT ET AL

It is certified that error appears in the above-identified patent and that said Letters Patent are hereby corrected as shown below:

In claim 1, column 8, line 27, insert a period (.) after "atoms" and delete the remainder of the claim.

Signed and Sealed this

Twenty-third Day of October 1979

[SEAL]

Attest:

RUTH C. MASON
*Attesting Officer*

LUTRELLE F. PARKER
*Acting Commissioner of Patents and Trademarks*